(12) United States Patent
Härkönen

(10) Patent No.: US 6,696,262 B2
(45) Date of Patent: Feb. 24, 2004

(54) METHOD FOR SCREENING THE RISK OF GASTRIC CANCER

(75) Inventor: Matti Härkönen, Espoo (FI)

(73) Assignee: Biohit Oyj, Helsinki (FI)

( * ) Notice: Subject to any disclaimer, the term of this patent is extended or adjusted under 35 U.S.C. 154(b) by 0 days.

(21) Appl. No.: 09/809,549

(22) Filed: Mar. 14, 2001

(65) Prior Publication Data

US 2001/0039025 A1 Nov. 8, 2001

Related U.S. Application Data

(63) Continuation of application No. 08/857,460, filed on May 16, 1997, now abandoned, which is a continuation-in-part of application No. PCT/FI95/00634, filed on Nov. 15, 1995.

(30) Foreign Application Priority Data

Nov. 16, 1994 (FI) .................................................. 945391

(51) Int. Cl.$^7$ ............................................ G01N 33/554
(52) U.S. Cl. ...................... 435/7.32; 435/7.23; 435/7.1; 435/7.4; 435/7.91; 435/7.72; 435/7.7
(58) Field of Search ........................... 435/7.1, 7.7, 7.4, 435/7.91, 7.72, 7.32, 7.23

(56) References Cited

U.S. PATENT DOCUMENTS 6,156,525 A * 12/2000 Furuta .......................... 435/7.4

OTHER PUBLICATIONS

Westerveld, BD et al, Cancer, vol. 59, 952–958, 1987.*
Webb, PM e tal, Gastroenterology, Nov. 1994, vol. 107(5), pp. 1335–1344.*
Maaroos, HI et al, Scand. J. Gastroenterol. vol. 29, pp. 532–536, 1994.*
Ardill, JES et al, Regulatory Peptides, vol. 40(2), pp. 109, year:1992, abstract only.*
Westerveld, BD et al, Pepsinogens in Man: Clinical and Genetic Advances, pp. 201–212, 1985.*
Petersen, B, Scand. J. Gastroenterol. (Norway), 1983, vol. 18(5), pp. 613–615.*
Petersen, B et al, Sancd. J. Gastroenterol..vol. 18, pp. 635–641, 1983.*
Walker, K etal, Clinical Therapeutics, vol. 7(6), pp. 704–716, 1985.*
Chen, TS et al, Am. J. Gastroenterol., Sep. 1994, vol. 89(9), pp. 1511–1514.*
Deprez, PH et al, Regulatory peptides, vol. 40(2), pp. 134, 1992.*
Janssen, M et al, Journal of Rheumatology, vol. 32, pp. 371–374, 1993.*
Karnes, WE et al, Gastroenterology, vol. 101, pp. 167–174, 1991.*
Mulholland, G et al, Gut, vol. 34, 1993, pp. 757–761 (best copy available).*
Newell, DG etal, Infect. Dis., vol. 3, pp. 1–6, 1989.*
Plebani, M, Crit. Rev. Clin. Lab. Sci, vol. 30(3), pp. 273–328, 1993.*
Sipponen, P et al, J. Clin. Pathology, vol. 45(4), pp. 319–323, 1992.*
Wu, WC et al, American J. Gastroenterology, vol. 89(8), p. 1361, 1994, abstract 304.*
Vol. 26, No 186, 1991, K. Varis et al., "Serum Pepsinogen I and Serum Gastrin in the Screening of Atrophic Pangastritis with High Risk of Gastric Cancer", pp. 117–123, see "Discussion", Scan. J. Gastroenterol.
Scand J Gastronenterol, vol. 26, No 186, 1991, M. Kekki et al, "Serum Pepsinogen I and Serum Gastrin in the Screening of Severe Atrophic Corpus Gastritis" pp. 109–116.
Cancer, vol. 59, 1987, B.D. Westerveld et al, "Clinical Significance of Pepsinogen A Isozymogens, Serum Pepsinogen A and C Levels, and Serum Gastrin Levels" pp. 952–958.
Dialog Information Service, file 154, Medline, Dialog accession No. 07951582, Medline accession No. 92089582, Farinati F. et al.: "Pepsinogen A/pepsinogen C or pepsinogen A multiplied by gastrin in the diagnosis of gastrin cancer", Ital J Gastroenterol (Italy) May 1991, 23 (4) p194–6.
Digestive Disease and Sciences, Vol 29, No 9, Sep. 1984, Haruka Sasaki et al, "Low Acid Output in Pima Indians A Possible Cause for the Rarity of Duodenal Ulcer in this Population", pp. 785–789.
Dialog Information Service, file 154, Medline, Dialog accession No. 08849602, Medline accession No. 94164602, Lin JT et al: "Serum levels of pepsinogen I and gastrin in gastric carcinoma: the influence of *Helicobacter pylori* infection and tumor characteristics", Hepatgastroenterology (Germany) Dec. 1993, 40 (6) p600–3.
Dialog Information Service, file 154, Medline, Dialog accession No. 08512746, Medline accession No. 93222746, Sitas F. et al: "Serum anti–*Helicobactor plyori* IgG antibodies and pepsinogens A and C as serological markers of chronic atrophic gastritis", Cancer Epidemiol Biomarkers Prev 1993, 2 (2) p119–23.
Clin. Chem., vol. 31, No. 1, 1985, Goran Lindstedt et al, "Analytical and Clinical Evaluation of a Radioimmunassay for Gastrin".

(List continued on next page.)

Primary Examiner—Lynette R. F. Smith
Assistant Examiner—Ginny Allen Portner
(74) Attorney, Agent, or Firm—Birch, Stewart, Kolasch & Birch, LLP

(57) ABSTRACT

Method for screening the risk for gastric cancer using, in combination, the determination of serum pepsinogen I, gastrin-17 and the supporting determination of *Helicobacter pylori* antibodies from blood serum, in order to detect either atrophy of the corpus area, atrophy of the antrum area or atrophy of the mucosa of the whole stomach as well as a causative *Helicobacter pylori* infection, whereby the risk for gastric cancer can be evaluated and the necessary gastroscopy and follow-up can be planned.

19 Claims, No Drawings

OTHER PUBLICATIONS

Int. J. Cancer, vol. 35, 1985, Pentti Sipponen et al., "Gastric Cancer Risk in Chronic Atrophic Gastritis: Statistical Calculations of Cross–Sectional Data" pp. 173–177.

Clinica Chimica Acta, vol. 162, 1987, Shih Che Huang et al, "Enzyme–linked immunosorbent assay of serum pepsinogen I" pp. 85–96.

Scan J Clin Lab Invest, Vol 47, 1987, Gerard Pals et al, "Enzyme–linked immunosorbent assay and radioimmunoassay of serum pepsinogen A" pp. 29–33.

Clinica Chimica Acta, vol. 175, 1988, Shih Che Huang et al, "Enzyme–linked immunsorbent assays for serum pepsinogens I and II using monoclonal antibodies—with data on peptic ulcer and gastric cancer" pp. 37–50.

Chemical Abstracts, vol. 119, 1993, 6252f, "Clinical Application of the determination of serum pepsinogens I and II levels and serum gastrin levels in gastroduodenal diseases", Nishi, S. et al. Wakayama Igaku 1992 43(2), 221–8 (Japan).

Tiivistelmä julkaisusta Jpn J Cancer Res (Japan), 84(8) s844–51, Aug. 1993, Kabuto M. et al., "Does high gastric cancer risk associated with low serum ferritin level reflect achlorhydria?" (English Abstract).

Tiivistelmä julkaisusta Ital J Gastroenterol (Italy), 23(4) s.194–6, May 1991, Farinati, F. et al., "Pepsinogen A/pepsinogen C or pepsinogen A multiplied by gastrin in the diagnosis of gastric cancer?" (English Abstract).

Tiivistelmä julkaisusta Dig Dis Sci (USA), 29(9) s.785–9, Sep. 1984, Sasaki, H. et al., "Low acid output in Pima Indians" (English Abstract).

Tiivistelmä julkaisusta Clin. Chem. vol. 31, 1985, no 1, s.76–82, Lindstedt, G. et al, "Analytical and clinical evaluation of a radio–immunoassay for gastrin" (English Abstract).

Chemical Abstracts, vol. 108, 1988, 69407d, "Plasma gastrin concentration, gastric content in antral mucosa and acid output in normal subjects and patients with gastrin cancer", Park, H. et al., Inkan Kwahak 1987, II(6), 359–66 (Korean) (English Abstract).

Chemical Abstracts, vol. 109, 1988, 106842k, "Enzyme–linked immunosorbent assay for serum pepsinogens I and II using monoclonal antibodies—with data on peptic ulcer and gastric cancer", Huang, S. et al., Clin. Chim. Acta 1988, 175(1), 37–50 (Eng.).

Chemical Abstracts, vol. 106, 1987, 171607q. "Enzyme–linked immunosorbent assay of serum pepsinogen I", Huang S., et al., Clin. Chim. Acta, 1987, 162(1), 85–96 (Eng.).

Chemical Abstracts, vol. 106, 1987, 151936t, "Enzyme–linked immunosorbent assay and radio–immunoassay of serum pepsinogen A", Pals, G. et al., Scand. J. Lab. Invest. 1987, 47(1) 29–33.

Clinical Chemistry, 3rd Ed., Mosby, 1995, p. 7 "Specificity and sensitivity".

Scand. J. Gastroenterol. 1991, 26(suppl 186), pp. 117–123 Varis et al "Serum pepsinogen I and serum gastrin in the screening . . . ".

* cited by examiner

METHOD FOR SCREENING THE RISK OF GASTRIC CANCER

CROSS REFERENCE TO RELATED APPLICATION

This application is a continuation application of Ser. No. 08/857,460, filed May 16, 1997 now abandoned, which is a continuation-in-part of PCT international application No. PCT/FI95/00634, which has an international filing date of Nov. 15, 1995, which designated the United States, the entire contents of which are hereby incorporated by reference.

BACKGROUND OF THE INVENTION

In the following background information is presented relating to methods for screening for the risk of gastric cancer, primarily using pepsinogen I and gastrin-17 determination from a blood sample.

Although the occurrence of new cases of gastric cancer has diminished in the recent years, gastric cancer is still one of the most common malignancies. In Finland, approximately 250 to 300 new cases of cancer/one million people/year are registered. In the age group of people above 50, there are an estimated 2350 cases of stomach cancer, which is about 3 per mille of the age group population (Finnish Cancer Registry—The Institute for Statistical and Epidemiological Cancer Research 1993). In addition to Finland, there is a high gastric cancer incidence in Iceland, South America and especially in Japan.

The prognosis of gastric cancer is usually poor, as there is no specific treatment. Presently the only possibility of successfully treating gastric cancer is its early detection and total removal surgically.

Gastric cancer does not necessarily give any symptoms in its early stages. The late appearance of symptoms naturally delays the patient from seeking treatment. On the other hand, the clinical findings in the early stage of gastric cancer are often non-specific. The primary diagnostic method for gastric cancer is presently gastroscopy and biopsies, cell and aspiration cytology associated therewith. As routine gastroscopies are carried out in order to examine symptoms, such as pain in the upper abdomen or bleeding of the gastrointestinal tract, a symptomatic gastric cancer discovered in this manner is often already far advanced and thus inoperable. Attempts have also been made at improving primary diagnostics with various immunological methods, but no sufficiently specific immunological method has been successfully developed.

It is a primary object to find the means by which it would be possible to identify within the general population easily and with moderate costs those symptomless persons which might be suffering from gastric cancer in its initial stages. After identification these persons should immediately be examined by gastroscopy. At the same time those persons could be identified which exhibit premalignant gastric changes which need to be followed up.

Gastric cancer can be preceded by a number of different gastric diseases or conditions (so called precancerous conditions), which are chronic atrophic gastritis, pernicious anaemia, ventricular ulcer, gastric polyposis and the Ménétrier disease (giant hypertrophic gastritis). Clearly identifiable changes of the mucosa are dysplasia and adenoma. The said conditions are associated with an approximate 4 to 5 fold relative cancer risk, as compared to the general population. It has been established that in almost all diseases the risk is mediated over chronic atrophic gastritis.

Chronic gastritis means a prolonged inflammatory condition of the gastric mucosa. The disease can coarsely be divided into the so-called superficial and the atrophic form. In superficial gastritis, the inflammatory cell infiltration is concentrated below the surface epithelium. In case the inflammation progresses and diffuses between the specific gastric secretory glands, one refers to chronic atrophic gastritis. In such a case, the normal glandular structures of the gastric mucosa are at least partly substituted by metaplastic changes.

The relative risk of gastric cancer in patients suffering from atrophic gastritis in the corpus area of the stomach, has been estimated, as calculated from the Finnish cancer statistics, to be about 4- to 5-fold as compared to persons having a healthy mucosa. In addition, there is a risk for falling ill with pernicious anaemia due to intrinsic factor deficiency and B12 vitamin absorption disturbance. In severe atrophy of the antrum area, the risk is even 18-fold. If atrophic changes appear both in the antrum and the corpus area (pangastritis), the risk can increase to even 90-fold (Sipponen, Kekki, Haapakoski, Ihamäki & Siurala 1985). Screening for Preliminary Stages of Gastric Cancer by Determination of Pepsinogen and Gastrin-17 in Serum Stomach Pepsinogens It is possible to electrophoretically distinguish 7 different pepsinogens from the gastric mucosa in humans (Samloff 1969). Of these the five fastest form the immunologically uniform group of pepsinogen 1. The other two form the pepsinogen II group. The group I pepsinogens are synthezised only in the main cells and the mucous secreting cells of the corpus area of the stomach. In contrast thereto, group II pepsinogens are formed in the glands over the whole stomach area and to some degree also in the upper part of the duodenum in the Brunner glands (Samloff & Liebman 1973; Weinstein, Lechango, Samloff et al 1977). In the serum of a healthy person the pepsinogen I concentration is approximately 6 times that of the pepsinogen II concentration (Samloff 1982). In atrophic gastritis of the corpus area of the stomach the serum pepsinogen I concentration decreases, whereas the serum pepsinogen II concentration remains at the previous level. Thus, the serum pepsinogen I concentration fairly well reflects the number of pepsinogen secreting cells in the corpus area of the stomach, and their condition. The more serious the atrophic gastritis of the corpus area of the stomach is, the lower is the serum pepsinogen I concentration (Tamm, Villako, Härkönen & Karonen 1984; Kekki, Samloff, Varis & Ihamäki 1991). A low pepsinogen I concentration in the serum indicates severe atrophic corpus gastritis with a sensitivity of over 90% and a specificity of almost 100% (Varis, Kekki, Härkönen, Sipponen & Samloff 1991).

In a Finnish study (Varis, Sipponen, Laxén, Härkönen & Heinonen, still unpublished) wherein symptom-free smoking men over the age of 50 were screened for gastroscopical examination based on a low serum pepsinogen I concentration, a neoplastic change was observed in 4.7% of those that had undergone gastroscopy (5.8% of the patients suffering from atrophic gastritis) and in 1% a symptom-free precancerous condition (Table 1 and Table 2) was observed. In this study it was possible to identify, based on the low serum pepsinogen I test result, a number of gastric cancer incidences requiring immediate surgery and pre-cancerous conditions (dysplasia) requiring subsequent gastroscopic following. At the same time it was possible to identify the population group which runs the risk of falling ill with pernicious anaemia and whose blood values should consequently be monitored in the future.

Epidemiological studies show that only about 25% of gastric cancer patients have severe atrophic corpus gastritis which can be verified based on a low serum pepsinogen I level (Sipponen, Kekki, Haapakoski; Ihamäki & Siurala 1985). In about 65% the cancer is preceded by atrophy in the antrum area, which thus is not verifiable by pepsinogen I determination.

TABLE 1

Results from a study for screening gastric cancer in Finnish smoking men over the age of 50, based on a low serum pepsinogen I (S-PG I) level

| Screening result | Number | % of the former | % of those gastroscopied |
|---|---|---|---|
| Number examined | 22431 | | |
| Low S-PG I | 2215 | 9.9 | |
| Gastroscopied | 1347 | 60.8 | |
| Atrophic corpus gastritis | 1092 | 81.1 | |
| Carcinoma | 63 | 5.8 | 4.7 |

TABLE 2

Neoplastic (tumour like) changes of the gastric mucosa based on pepsinogen I determination in men over 50 years of age examined in Finland (see Table 1).

| Neoplastic type | Number |
|---|---|
| Moderate dysplasia (abnormal growth) | 42 |
| Severe dysplasia | 7 |
| Carcinoma | 11 (initial 70%) |
| Carcinoid tumour | 3 |
| Total number | 63 |

Gastrin of the Antrum Area

Gastrin is secreted in the gastrointestinal tract in at least three different forms, the immunoreactive activity of all these forms being measured when serum gastrin is determined (total serum gastrin). Gastrin subtypes are the so-called minigastrin (G-14), little gastrin (G-17) and big gastrin (G-34) (Gregory 1974). Physiologically most important are gastrin-17 and gastrin-34. The effect of gastrin-17 on the secretion of hydrochloric acid is 6 times that of gastrin-34 (Walsh, Isenberg, Ansfield & Maxwell 1976). Gastrin is secreted from the so-called G-cells, which appear both in antrum and in duodenum. The most important accelerators of gastrin secretion is the tonus of the vagus nerve and the protein degradation products. The secretion of gastrin is slowed down by a pH decrease of below 2.5 (Walsh, Richardson & Fordtran 1975). The gastrin secreted from the antrum is to over 90% of the gastrin-17 type, whereas the duodenal gastrin is primarily of the gastrin-34 type (Berson & Yalow 1971). In a fasting situation, primarily gastrin-34 is found in the serum, whereas after a meal the serum gastrin is of the gastrin-17 type (Lamers, Harrison, Ippoliti & Walsh 1979). The secretion of gastrin-17 can also be studied using the so-called protein stimulation test. In such a test, a blood sample after fasting is taken in the morning, whereafter the patient eats a protein rich standard meal and blood samples are taken at 15 minute intervals for two hours. The maximal increase is evident after appr. 20 minutes.

In atrophic antrum gastritis the mucous membrane of the antrum is atrophied and thus its gastrin-17 secretion decreases and its concentration in the serum is reduced. A reduced gastrin-17 concentration in the serum would thus be an indicator of antrum atrophy and of an increased risk for cancer in this area. In case the mucous membrane of the antrum is atrophied, there is a reduced response also in the protein stimulation test, which seems to be a more sensitive indicator of atrophy than the mere concentration determination.

Helicobacter pylori Infection of the Stomach

Helicobacter pylori is a spiral shaped, gram-negative bacterium which thrives in the mucus in the immediate vicinity of the surface epithelial cells of the gastric mucosa and in the cell interstices. The bacterium apparently is transferred perorally from one person to the other. The effect of the bacterium on the gastric mucosa is an inflammation reaction, which is mediated over a complement by liberating strong inflammation mediator substances. After the acute stage, the inflammation is transformed into chronic gastritis. In patients suffering from chronic gastritis, in 70 to 90% a Helicobacter pylori infection can be established (Calam 1994). As Helicobacter pylori infection and chronic gastritis in the stomach are closely associated, it has been stipulated that this bacterial infection could be one etiological factor in the development of stomach cancer. It is for this reason possible that eradication of the Helicobater pylori bacteria in the initial stages of the infection, could prevent the development of atrophy associated with chronic gastritis, and thus reduce the cancer risk.

Screening for Gastric Cancer Using Combined Pepsinogen I—Gastrin-17-Helicobacter pylori-Antibody Determination in Serum For the screening preferably a method can be used, according to which on a microplate simultaneously the serum pepsinogen I and gastrin-17 concentration and the Helicobacter pylori antibodies can be determined. It is hereby possible to diagnose either corpus gastritis, antrum gastritis or pangastritis, as well as one cause of atrophy, Helicobacter pylori infection. It is to be noted that in severe atrophic gastritis, no Helicobacter pylori bacteria can be found in the gastric mucosa, and also the antibodies in the serum have been normalized.

For pepsinogen I determination the pepsinogen I antigen has been purified from the human gastric mucosa. It has been coupled by thiolation and protein-protein-conjugation to rabbit or sheep red blood cells and so rabbits or sheep have been immunized in the classical manner to produce antibodies to pepsinogen I. A polyclonal antibody to gastrin-17 has been produced with the same technique by coupling a [Leu$^{15}$]-gastrin-17 (Sigma S-9145, [Leu$^{15}$]-gastrin-I) or the gastrin-17 fragment 1–13 (Sigma G-6261) to rabbit autological red blood cells and immunizing the rabbits in a normal manner the rabbits to produce a specific antibody to gastrin-17. Polyclonal antibodies have been produced also with BSA-conjugates in the classical manner. A monoclonal gastrin-17 antibody has been produced in the classical manner in mouse with a [Leu$^{15}$]-gastrin-17-derivative, which is conjugated to thyroglobulin. The specific antibodies have been purified with protein A-affinity chromatography or in some cases with pepsinogen I or gastrin-17 affinity chromatography.

Pepsinogen I Determination

1. The microplate wells are coated with a polyclonal antibody by incubating over night at +4° C.
2. The wells are emptied and washed with a washing solution.
3. The sample is added at a suitable dilution, and incubated at the most one hour at +37° C.
4. The wells are washed.
5. The enzyme labelled monoclonal antibody is added at a suitable dilution, and incubated for at the most one hour at +37° C.

6. The wells are washed.
7. The substrate is added (chromogenic, fluorescent or luminescent substrate), and incubated maximally for 30 mins at room temperature.
8. The reaction is stopped and the absorbance, fluorescence or luminescence is determined and compared to a calibration curve.

The method can be speeded up by incubating the sample and the enzyme labelled monoclonal antibody simultaneously as a so-called one-step-ELISA-method. There are also other alternatives that can be used.

Alternative 2 (Competitive ELISA)

1. The sample and antibody are incubated on microplate wells, whereby the antigen of the sample couples to the antibody.
2. A known amount of labelled antigen is added, which competes with the antigen in the specimen for free antibody.
3. The solution is transferred to a microplate well which has been coated with a second antibody, and incubated maximally for 1 hour.
4. Unbound material is washed away.
5. The substrate is added and incubated maximally for 30 minutes at room temperature.
6. The reaction is stopped and the results are evaluated by comparing to calibration curve.

As an alternative, the antigens can be added simultaneously and/or directly to a microplate well coated with a second antibody, but in such a case the sensitivity of the process is not as good. In this process, the competition can be arranged also with labelled antibody.

Gastrin-17 Determination

1. The wells are coated with streptavidin.
2. An excess of gastrin-17 derivative labelled with biotin is added and incubated until equilibrium is reached.
3. The sample and the monoclonal antibody are added whereby the gastrin-17 in the specimen and the biotin labelled gastrin-17 compete for the antibody. The mixture is incubated for one hour at +37° C.
4. The wells are washed.
5. The enzyme labelled second antibody is added and incubated for appr. one hour.
6. The substrate (fluorescent or luminescent) is added and incubated for appr. 30 minutes at room temperature.
7. The reaction is stopped and the fluorescence or luminescence is read, and compared to a calibration curve.

*Helicobacter pylori* Determination

For the determination of the *Helicobacter pylori* antibodies a number of commercial "kits" are available (e.g. Orion Pyloriset EIA-G, Pyloriset EIA-A, EIA 2G by Roche, Pyloristat by Whittaker Bioproducts). Antigens can be prepared from *Helicobacter pylori* bacteria in various ways (see Lelwala-Guruge, Nilsson, Ljungh, Wadström 1992) and they are also commercially available. The method we use for determining *Helicobacter pylori* antibodies is generally known and the antigen extracted from the bacteria with acidic glycine is attached by adsorption to the wells in a microplate. The second antibody (rabbit anti-human IgG) is labelled with enzyme (alkaline phosphatase and in some cases peroxidase). p-Nitrophenyl phosphate (adsorbance) or umbelliferyl-phosphate (fluorescence) is used as the enzyme substrate, whereby the absorbance (405 nm) or fluorescence (360 nm/460 nm) can be measured.

Sensitivity of Measurement

In the determination of serum pepsinogen I the cut-off-value for atrophic gastritis is, according to our previous studies, 20–30 μg/l depending on the specificity and sensitivity agreed upon for the method in question, which corresponds to appr. 450–690 pmol/l (Varis, Sipponen, Laxén, Härkönen & Heinonen, still unpublished). In a normal situation the gastrin-17 concentrations are in the range of 2–25 pmol/l. Thus, the serum gastrin-17 concentration is appr. 100 times smaller than that of pepsinogen I. As one measures even lower values in atrophic antrum gastritis, a very high sensitivity of the developed method is required. In atrophy of the antrum area the cut-off value for serum gastrin-17 determination is in the range of 0.1–2 pmol/l. It is possible to reach a sufficiently high sensitivity with an enzyme label and using, for example, luminescence measurement as a sensitive detection system. The sensitivity can be further increased by performing a so-called enzymatic recycling reaction which we have applied i.a. for the determination of steroids (Härkönen, Adlercreutz & Groman 1974). Also in this case the product formed can be measured either using fluorescence technique or luminescence. For the *Helicobacter pylori* positiveness the cut-off titer is 200–500. The use of the combination method for detecting atrophy of the mucosa in the various parts of the stomach is shown in the Table 3.

TABLE 3

Combination method for serum pepsinogen I and gastrin-17 for detecting severe atrophic gastritis of the mucosa of the corpus area or the antrum area of the stomach, or of the whole stomach (pangastritis).

| Location of severe atrophy in stomach | Serum pepsinogen I μg/l | Serum gastrin-17 pmol/l | Increase of serum gastrin-17 (response) in protein stimulation |
|---|---|---|---|
| Corpus | < cut-off value | > upper limit | normal or increased response |
| Antrum | | > cut-off value | < cut-off value | strongly reduced response |
| Mucosa of the whole stomach (corpus and antrum) | < cut-off value | < cut-off at the lower limit of reference value | reduced response |

Reference values:
Serum pepsinogen I 25–120 μg/l
Serum gastrin-17 2–25 pmol/l
Cut-off-values:
Serum pepsinogen I 20–30 μg/l
Serum gastrin-17 0.1–2 pmol/l According to the Table 3, when the serum pepsinogen I concentration is below the cut-off value, which according to the specificity of the method is in the range of approximately 20–30 μg/l, the atrophy is located in the corpus area of the stomach. If, on the other hand, the serum gastrin-17 concentration is below the cut-off value, which depending on the specificity of the method is in the range of 0.1–2 pmol/l, the atrophy is located in the antrum area of the stomach. In atrophy of the corpus area the gastrin-17 value is above the upper limit of the reference values. Correspondingly in pangastritis, the serum pepsinogen I concentration is below the cut-off value whereas the gastrin-17 concentration is at the lower limit of the reference values. The location of the atrophy can also be verified using the protein stimulation test, in which the serum gastrin-17 concentration is measured at the base line situation and after a protein rich standard meal. The response (increase of serum gastrin-17 as compared to the base line situation) is strongly reduced in atrophy of the antrum area only, and slightly decreased in atrophy of the mucosa of the whole stomach. On the other hand, if the mucosa of the antrum is healthy, but the corpus area is atrophied, the response is normal or increased.

Kits According to the Invention

The present invention further relates to a kit for screening for the risk of gastric cancer. The kit can comprise a combination of the individual components needed to quantitatively determine the pepsinogen I and gastrin-17 concentrations in a blood serum sample. For this purpose, the kit can comprise separate vials or containers for the necessary antibodies (labelled and unlabelled), antigens and substrates, or a support in the form of a microplate well, allowing, for example, the simultaneous determination of pepsinogen I and gastrin-17. The kit may also contain the components necessary for determining the amount of H. pylori antibodies in a sample.

Enzyme Immunoassay

1) Gastrin-17 monoclonal antibodies were produced conventionally (Köhler & Milstein, 1975) by immunizing BAL/c mice with {Leu$^{15}$}-gastrin-17 (Sigma) coupled to bovine thyroglobulin (Sigma). Ten positive hybridomas were used for ascites production and monoclonal antibodies were purified from ascites fluid using Protein A Sepharose (Pharmacia) and ammonium sulphate precipitation. Antibody titers were tested by coating microwell plates (Nunc) with BSA-conjugated gastrin-17 (5 μg/ml). The cross-reaction of antibodies with gastrin-34 was tested by coating microwell plates with BSA-conjugated gastrin-34 (5 μg/ml). An antibody clone with high affinity for gastrin-17 and very low cross-reaction with gastrin-34 was chosen for enzyme immunoassay. The monoclonal antibody was conjugated with alkaline phosphatase (Boehringer Mannheim) using the two-step procedure with glutaraldehyde (according to working instruction of Boehringer Mannheim). Gastrin-17 was biotinylated classically with N-hydroxy-succinimidibiotin (Pierce) and dialysed against 0.5 M carbonate buffer pH 9.5 in Spectra/Por 6 MWCO 1000 dialysis membrane (Spectrum Medical Industries Inc.). Biotinylated gastrin-17 was further purified with size exclusion chromatography using Superdex peptide HR 10/30 column (Pharmacia Biotech).

Gastrin-17 enzyme immunoassay (EIA) is based on competition between gastrin-17 in the serum sample and biotinylated gastrin-17 (e.g. von Grüningen et al., 1991). Microwell plates are coated with streptavidin (1 μg/ml) in carbonate buffer, pH 9.6. Sample, biotinylated gastrin-17 and alkaline phosphatase conjugated monoclonal antibody are incubated simulataneously 30 min at 37° C. After wash with 0.02 M PBS containing 0.05% Tween 20 chemiluminescence substrate AMPPD (Tropix Inc., Bedford Mass., U.S.A.) is pipetted on the plate and the signal is detected after 10 min incubation at room temperature with a chemiluminescence microtiter plate reader.

2) For measuring pepsinogen I (PGI) in serum we have developed a sandwich enzyme immunoassay (EIA) method using monoclonal antibodies produced in a concentional way (Köhler & Milstein, 1995) against human PGI purified from stomach. The microwell plates are coated overnight at 4° C. with monoclonal antibody (3 μg/ml in PBS) and washed three times with 0.02 M PBS, 0.05% Tween 20, pH 7.0. The sample is diluted 1:50 in 13 mM phosphate buffer, pH 7.5 containing 22 mM EDTA and 0.3% BSA and applicated on the plate. The samples are incubated 30 min at 37° C. and the plates are washed as described. Second antibody, conjugated with horseradish peroxidase (HRP), is diluted 1:100 in 13 MM phosphate, pH 7.5, 22 mM EDTA, 0.3% BSA and applicated on the plate. The plates are incubated 30 min at 37° C. and washed as described. After wash the substrate, 3,3',5,5'-tetramethylbenzidin (Merck), is applicated and plates are incubated 30 min at room temperature after which the reaction is stopped with 2 M sulphuric acid. The absorbance is measured at the wavelength 450 nm with Anthos reader 2001 (Anthos Labtec Instruments, Austria). For the calculation of the results, the polynomial fitting curve of $3^{rd}$ degree was used. The detection limit of this method is 1.5 μg/l, in serum. Within assay variation measured with sample concentration 67.2 μg/l is 5.4% and between assay variation measured with sample concentration 21.6 μg/l is 7.6%.

LITERATURE

Berson S A & Yalow, R S (1971) Nature of immunoreactive gastrin extracted from tissues of gastrointestinal tract. Gastroenterology 60:215–222

Calam, J (1994) Helicobacter pylori (Review) Eur. J. Clin Invest 24: 501–510

Gregory, R A (1974) The gastrointestinal hormones; a review of recent advances, J. Physiol. 241: 1–32

The Finnish Cancer Registry—The Institute for Statistical and Epidermiological Cancer Research (1993) Cancer Incidence in Finland 1991. Cancer Statistics of the National Research and Development Centre for Welfare and Health Härkönen, M, Adlercreutz, H & Groman, EV (1974) Enzymatic techniques in steroid assay. J. Steroid Biochem. 5: 717–725

Kekki, M, Samloff, I M, Varis, K & Ihamäki, T (1991) Serum pepsinogen I and serum gastrin in the screening of severe atrophic corpus gastritis. Scand J Gastroenterology 26 (suppl 186):109–116

Lamers, C, Harrison, A, Ippoliti, A & Walsh, J (1979) Molecular forms of circulating gastrin in normal subjects and duodenal ulcer patients. Gastroenterology 76: 1179

Lelwala-Guruge, J, Nilsson, I, jungh, Å & Wadström. T (1992) Cell surface proteins of Helicobacter pylori as antigens in an ELISA and a comparison with three commercial ELISA. Scand J Infect Dis 24: 457–465

Samloff, J M & Liebman, W M (1972) Purification and immunochemical characterization of group II pepsinogens in human seminal fluid. Clin Exp Immunol 11:405–414

Samloff, I M (1969) Slow moving protease and the seven pepsinogens. Electrophoretic demonstration of the existence of eight proteolytic fractions in human gastric mucosa. Gastroenterology 57:659–69

Samloff, I M (1982) Pepsinogens I and II: purification from gastric mucosa and radioimmuno-assay in serum. Gastroenterology 82:26–33

Sipponen, P, Kekki, M, Haapakoski, J. Ihamäki, T & Siurala, M (1985) Gastric cancer risk in chronic atrophic gastritis: statistical calculations of cross-sectional data. Int J Cancer 35:173–77

Tamm, A, Villako, H, Harkonen, M & Karonen, S-L (1984) Serum pepsinogen I and the state of gastric mucosa in an Estonian population sample. Scand. J. Gastroenterol, 19: 1091–1094.

Varis, K (1993) Secretorial function of the stomach (Mahan eritystoiminta) in the book Clinical gastroenterology (Kliininen gastroenterologia) editor (toim.) Miettinen, T. Seppälä, K & Sivula, A., Duodecim, Jyväskylä pp. 55–69

Varis, K, Kekki, M, Härkönen, M, Sipponen, P & Samloff, I M (1991) Serum pepsinogen I and serum gastrin in the screening of atrophic pangastritis with high risk of gastric cancer. Scand J Gastroenterology 26 (suppl 186): 117–123

Varis, K, Sipponen, P, Laxén, F. Härkönen, M & Heinonen O-P, julkaisematon työ.

Walsh, J H, Isenberg J I, Ansfield, J & Maxwell, V (1976) Clearance and acid-stimulating action of human big and little gastrins in duodenal ulcer subjects. J Clin Invest 57: 1125–1131

Walsh, J H, Richardson, C T & Fordtran, J S (1975) pH dependence of acid secretion and gastrin release in normal and ulcer subjects. J Clin Invest 55: 462–468

Weinstein, W M, Lechago, J. Samloff, I M et al. (1977) Pepsinogens in human gastric and esophageal glands (abstr). Clin Res 25:690

What is claimed is:

1. A method for screening for atrophy of the corpus of the stomach from blood serum, such atrophy correlating with increased risk of gastric cancer, said method comprising:
   a) obtaining a serum sample from a patient;
   b) quantitatively measuring the pepsinogen-I from said serum sample using an immunoassay and comparing the value obtained to a cut-off value for pepsinogen-I selected from a range of approximately 20–30 µg/l, which overlaps the lower end of the reference range of approximately 25–120 µg/l; and
   c) quantitatively measuring the gastrin-17 concentration from said serum sample by immunoassay and comparing the values obtained to a reference range of approximately 2–25 pmol/l for gastrin-17,
   whereby a pepsinogen-I concentration in said serum sample below the cut-off value in combination with a gastrin-17 above the upper reference limit is indicative of atrophy of the corpus area of the stomach.

2. A method for screening for atrophy of the mucosa of the whole stomach from blood serum, such atrophy correlating with increased risk of gastric cancer, which comprises:
   a) obtaining a serum sample from a patient,
   b) quantitatively measuring the pepsinogen-I from said serum sample using an immunoassay and comparing the value obtained to a cut-off value for pepsinogen-I selected from a range of approximately 20–30 µg/l, which overlaps the lower end of the reference range of approximately 25–120 µg/l; and
   c) quantitatively measuring the gastrin-17 concentration from said serum sample and comparing the value obtained to a reference range of 2–25 pmol/l for gastrin-17,
   whereby a pepsinogen-I concentration in said serum sample below the pepsinogen-1 cut-off value and a gastrin-17 concentration in said serum sample within the reference range for gastrin-17 is indicative of atrophy of the mucosa of the whole stomach.

3. The method according to claim 1 or 2, further comprising a protein stimulation test that measures serum gastrin-17 concentration after fasting and then after a protein rich standard meal.

4. The method according to claim 1 or 2, wherein said immunoassay is conducted with an enzyme labeled antibody and a chromogenic, fluorescent or luminescent substrate, and absorbance, fluorescence or luminescence is measured.

5. The method according to claim 1 or 2, wherein said pepsinogen-I immunoassay is performed using polyclonal or monoclonal antibodies which specifically bind to said pepsinogen-I.

6. The method according to claim 1 or 2, wherein said gastrin-17 immunoassay is performed using polyclonal or monoclonal antibodies which specifically bind to said gastrin-17.

7. The method according to claim 6, wherein a polyclonal antibody to gastrin-17 is obtained by immunizing an animal with the gastrin fragment 1–13, $\{Leu^{15}\}$-gastrin-17 or using a gastrin-17 antigen isolated from the stomach of an animal.

8. The method according to claim 6, wherein said monoclonal antibodies are mouse monoclonal antibodies which specifically bind to $\{Leu^{15}\}$-gastrin-17 antigen.

9. The method according to claim 1 or 2, further comprising an immunoassay to detect the presence of *Helicobacter pylori* antibodies.

10. A method for screening for atrophy of the antrum area of the stomach from blood serum such atrophy correlating with increased risk of gastric cancer, which comprises:
    a) obtaining a blood serum sample from a patient
    b) quantitatively measuring the pepsinogen-I concentrations using an immunoassay and comparing the value obtained to a cut-off value for pepsinogen-I selected from the range of approximately 20–30 µg/l, which overlaps the lower end of the reference range of approximately 25–120 g/l; and
    c) quantitatively measuring the gastrin-17 concentration from said serum sample by immunoassay and comparing it to a cut-off value for gastrin-17 selected from a range of approximately 0.1–2 pmol/l, which is below the reference range of approximately 2–25 pmol/l
    whereby a pepsinogen I concentration above said cut-off value in combination with a gastrin-17 concentration in said sample below said cut-off value is indicative of atrophy of the antrum area of the stomach.

11. The method according to claim 10, further comprising a protein stimulation test that measures serum gastrin-17 concentrations after fasting and then after a protein rich standard meal.

12. The method according to claim 10, wherein said immunoassay is conducted with an enzyme labeled antibody and a chromogenic, fluorescent or luminescent substrate, and absorbance, fluorescence or luminescence is measured.

13. The method according to claim 10, wherein said immunoassay for said pepsinogen-I concentration is performed using polyclonal or monoclonal antibodies which specifically bind to pepsinogen-I.

14. The method according to claim 10, further comprising an immunoassay to detect the presence of *Helicobacter pylori* antibodies.

15. The method according to claim 10, wherein said immunoassay for said gastrin-17 concentration is performed using polyclonal or monoclonal antibodies which specifically bind to gastrin-17.

16. The method according to claim 15, wherein a polyclonal antibody to gastrin-17 is obtained by immunizing an animal with the gastrin fragment 1–13, $\{Leu^{15}\}$-gastrin-17 or using a gastrin-17 antigen isolated from the stomach of an animal.

17. The method according to claim 16, wherein said monoclonal antibodies are mouse monoclonal antibodies which specifically bind to $\{Leu^{15}\}$-gastrin-17 antigen.

18. A method for screening for atrophy of the corpus of the stomach from blood, serum or plasma, such atrophy correlating with increased risk of gastric cancer, said method comprising:
    a) obtaining a blood, serum or plasma sample from a patient;
    b) quantitatively measuring the pepsinogen-I from said sample using an immunoassay and comparing the value obtained to a cut-off value for pepsinogen-I selected from a range of approximately 20–30 µg/l, which overlaps the lower end of the pepsinogen-I reference range of approximately 25–120 µg/l; and c) quantitatively measuring the gastrin-17 concentration from serum sample by immunoassay and comparing the values obtained to a reference range of approximately of 2–25 pmol/l for gastrin-17, whereby a pepsinogen-I concentration in said sample below the pepsinogen-I cut-off value in combination with a gastrin-17 above the upper gastrin-17 reference limit is indicative of atrophy of the corpus area of the stomach.

19. A method for screening for atrophy of the mucosa of the whole stomach from blood, serum or plasma, such atrophy correlating with increased risk of gastric cancer which comprises:

a) obtaining a blood, serum or plasma sample from a patient, b) quantitatively measuring the pepsinogen-I from said sample using an immunoassay and comparing the value obtained to a cut-off value for pepsinogen-I selected from a range of approximately 20–30 µg/l, which overlaps the lower end of the reference range of approximately 25–120 µg/l; and c) quantitatively measuring the gastrin-17 concentration from said sample and comparing the value obtained to a reference range of 2–25 pmol/l for gastrin-17, whereby a pepsinogen-I concentration in said sample below the pepsinogen-1 cut-off value and a gastrin-17 concentration in said serum sample within the reference range for gastrin-17 is indicative of atrophy of the mucosa of the whole stomach.

* * * * *